US012799450B2

(12) United States Patent
Yan et al.

(10) Patent No.: US 12,799,450 B2
(45) Date of Patent: Nov. 17, 2026

(54) **HIGHLY EFFICIENT TANNIN-DEGRADING STRAIN SL006 FROM *ROSA ROXBURGHII* AND APPLICATION THEREOF**

(71) Applicant: Liupanshui Normal University, Liupanshui (CN)

(72) Inventors: Kai Yan, Liupanshui (CN); Xiaoyong Zhang, Liupanshui (CN); Jianhong Li, Liupanshui (CN); Guimei Zhang, Liupanshui (CN)

(73) Assignee: Liupanshui Normal University, Liupanshui (CN)

( * ) Notice: Subject to any disclaimer, the term of this patent is extended or adjusted under 35 U.S.C. 154(b) by 484 days.

(21) Appl. No.: 18/460,928

(22) Filed: Sep. 5, 2023

(65) Prior Publication Data

US 2024/0218314 A1 Jul. 4, 2024

Related U.S. Application Data

(63) Continuation of application No. PCT/CN2023/104434, filed on Jun. 30, 2023.

(30) Foreign Application Priority Data

Dec. 29, 2022 (CN) ......................... 202211709689.6

(51) Int. Cl.

| | |
|---|---|
| ***C12R 1/80*** | (2006.01) |
| ***C12N 1/14*** | (2026.01) |
| ***C12N 1/145*** | (2026.01) |
| ***C12P 7/22*** | (2006.01) |
| ***C12R 1/645*** | (2006.01) |

(52) U.S. Cl.

CPC . *C12N 1/14* (2013.01); *C12P 7/22* (2013.01)

(58) Field of Classification Search

None

See application file for complete search history.

(56) References Cited

U.S. PATENT DOCUMENTS 5,691,173 A 11/1997 Primrose et al.

FOREIGN PATENT DOCUMENTS

| | | |
|---|---|---|
| CN | 105884545 A | 8/2016 |
| WO | 2004005275 A1 | 1/2004 |

OTHER PUBLICATIONS

First Office action for China Application No. 202211709689.6, mailed May 8, 2023.

Yan Kai et al., "Ascorbic Acid 6% As Inducing Resistance against *Sphaerotheca* sp. in Rosa roxburghii Tratt," Agrochemicals, Jul. 2017, vol. 56, No. 7.

Cheng Juan et al., "Microbial degradation of Zhaotong lignite to increase the content of free humic acid," Jiangsu Agricultural Science, Jan. 2020, pp. 296-301, vol. 48, No. 17.

Lan Ping et al., "Microbial degradation of grape pomace tannins," Journal of Forestry Engineering, Jan. 2017, pp. 58-63, vol. 2, No. 5.

Luo Xin, "Microbial Degradation of Larch Tannin to Catechin," Food Science, Apr. 2006.

Vidyasagar G M et al., "Penicillium citrinum Thom: A potential antihyperglycemic endophyte from Gymnema sylvestre," Indian Journal of Natural Products and Resources, Dec. 2021, pp. 557-563, vol. 12, No. 4.

*Primary Examiner* — S. Devi

(74) *Attorney, Agent, or Firm* — Pilloff Passino & Cosenza LLP; Rachel K. Pilloff; Sean A. Passino

(57) ABSTRACT

A strain of highly efficient tannin-degrading bacterium SL006 from *Rosa roxburghii* and application thereof are disclosed in the present application, belonging to the technical field of biotechnology. The highly efficient tannin-degrading bacterium SL006 from *Rosa roxburghii* has a taxonomic designation of *Penicillium adametzioides*, and has been preserved in the China Center for Type Culture Collection (CCTCC), with a preservation number of CCTCC NO:M 20221946. The highly efficient tannin-degrading bacterium SL006 with high tannin degradation efficiency is separated, purified and screened from moldy *Rosa roxburghii* pomace.

7 Claims, 19 Drawing Sheets

Specification includes a Sequence Listing.

SEQUENCE LISTING

```
Sequence total quantity: 6
SEQ ID NO: 1            moltype = DNA  length = 24
FEATURE                 Location/Qualifiers
source                  1..24
                        mol_type = other DNA
                        organism = synthetic construct
SEQUENCE: 1
ggtaaccaaa tcggtgctgc tttc                                         24

SEQ ID NO: 2            moltype = DNA  length = 24
FEATURE                 Location/Qualifiers
source                  1..24
                        mol_type = other DNA
                        organism = synthetic construct
SEQUENCE: 2
accctcagtg tagtgaccct tggc                                         24

SEQ ID NO: 3            moltype = DNA  length = 19
FEATURE                 Location/Qualifiers
source                  1..19
                        mol_type = other DNA
                        organism = synthetic construct
SEQUENCE: 3
tccgtaggtg aacctgcgg                                               19

SEQ ID NO: 4            moltype = DNA  length = 20
FEATURE                 Location/Qualifiers
source                  1..20
                        mol_type = other DNA
                        organism = synthetic construct
SEQUENCE: 4
tcctccgctt attgatatgc                                              20

SEQ ID NO: 5            moltype = DNA  length = 451
FEATURE                 Location/Qualifiers
source                  1..451
                        mol_type = other DNA
                        organism = synthetic construct
SEQUENCE: 5
ctgctttctg gtacgtgttt ccacccatca aatgttgaca cccattgaaa ctttttact  60
aactacctta taggcagaac attgcctccg agcacggtct cgatggtgat ggacagtaag  120
ttctttgatt cgagtcgatt ggtatatatg gtgggaatgg cggtctgata ttttttttct  180
agcttcaccg gccagtccga cctccagctg gagcgtatga acgtctactt caaccacgta  240
agtgtggaat tgatccctcg agccattcga tattggctaa tatttggatt gtttacaggc  300
cagcggtgac cgttacgttc cccgtgccgt cctggtcgat ttggagcccg gtaccatgga  360
cgctgtccgt gccggtcctt tcggcaagct tttccgtccc gacaacttcg ttttcggtca  420
gtccggtgct ggtaacaact gggccaaggg t                                 451

SEQ ID NO: 6            moltype = DNA  length = 540
FEATURE                 Location/Qualifiers
source                  1..540
                        mol_type = other DNA
                        organism = synthetic construct
SEQUENCE: 6
cattactgag tgagggcctt cgggtccaac ctcccacccg tgtctattgt accatgttgc  60
ttcggcaggc ccgccttatg gccgccgggg gctaaccgcc ccgggcccgc gcctgccgaa  120
gacccctctg aacgctgtct gaagattgcc gtctgagcga aacatataaa ttatttaaaa  180
ctttcaacaa cggatctctt ggttccggca tcgatgaaga acgcagcgaa atgcgataac  240
taatgtgaat tgcagaattc agtgaatcat cgagtctttg aacgcacatt gcgccctctg  300
gtattccgga gggcatgcct gtccgagcgt cattgctgcc ctcaagcccg gcttgtgtgt  360
tgggtctcgt cccccccggg ggacgggccc gaaaggcagc ggcggcaccg tgtccggtcc  420
tcgagcgtat ggggctttgt cacccgctct gtaggcccgg ccggcgcctg tcgaccccca  480
atctattttt ttcaggttga cctcggatca ggtagggata cccgctgaac ttaagcatat  540
```

HIGHLY EFFICIENT TANNIN-DEGRADING STRAIN SL006 FROM *ROSA ROXBURGHII* AND APPLICATION THEREOF

CROSS-REFERENCE TO RELATED APPLICATIONS

This application is a continuation of PCT/CN2023/104434, filed on Jun. 30, 2023 and claims priority to Chinese Patent Application No. 202211709689.6, filed on Dec. 29, 2022, the entire contents of which are incorporated herein by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:

File name: sequence_347_036_2023_8659
Creation date: Aug. 9, 2023
Byte size: 7,134

TECHNICAL FIELD

The present application relates to the field of biotechnology, and in particular to a strain of highly efficient tannin-degrading strain SL006 from *Rosa roxburghii* and application thereof.

BACKGROUND

*Rosa roxburghii* (scientifically named *Rosa roxburghii* Tratt) is rich in vitamin C, polyphenols, polysaccharides, flavonoids and other substances, of which vitamin C, flavonoids and superoxide dismutase (SOD) are extremely abundant, making the fruit known as the "fruit containing the most vitamin C, flavonoids and SOD". Among the provinces where *Rosa roxburghii* is planted, Guizhou enjoys the largest *Rosa roxburghii* planting area in the country, reaching 140000 hectares and fresh fruit production 130,000 tons by 2021. In the meantime, as the continued expansion of the deep processing industry of *Rosa roxburghii*, tens of thousands of tonnes of pomace are produced every year, which, if not properly handled, will cause the problems of resource wastage and environmental pollution. The pomace of *Rosa roxburghii* after juicing still contains rich nutrients, available for processing organic fertilizers, food, health care products, and livestock and poultry feed. However, the tannins contained in the pomace of *Rosa roxburghii* have anti-nutritional side effects, including suppressing the growth of the plant root system. Methods of plant tannin degradation mainly include physical degradation, chemical degradation and biodegradation, of which biodegradation has the advantages of less pollution, higher efficiency, etc., and is widely used in the desiccation process of food, feed and organic fertilizers. Thus, the present application provides a new highly efficient tannin-degrading strain for the industrial organic fertilizer fermentation of *Rosa roxburghii* pomace.

SUMMARY

The present application aims to provide a strain of highly efficient tannin-degrading strain SL006 from *Rosa roxburghii* and application thereof, so as to solve the problems existing in the above mentioned prior art; the strain has a high tannin degradation efficiency of up to 98.31%, while by improving fermentation conditions and formulations, the degradation of tannin within the pomace of *Rosa roxburghii* by the strain SL006 reaches more than 95%, which is of great significance in improving the quality of organic fertilizer fermentation of *Rosa roxburghii* pomace.

In order to achieve the above objectives, the present application provides following technical schemes:

the present application provides a strain of highly efficient tannin-degrading strain SL006 from *Rosa roxburghii*, with a taxonomic designation of *Penicillium adametzioides*, and has been preserved in the China Center for Type Culture Collection (CCTCC), with a preservation number of CCTCC NO: M 20221946, a preservation address of Wuhan University of China, and a preservation date of Dec. 13, 2022. The place of collection is Lipanshui, Guizhou, China.

The present application also provides a microbial agent, including the highly efficient tannin-degrading strain SL006 from *Rosa roxburghii*.

The present application also provides an application of the highly efficient tannin-degrading strain SL006 from *Rosa roxburghii* or the microbial agent in tannin degradation.

The present application also provides a method for degrading tannin, including a step of fermenting the tannin-degrading strain SL006 from *Rosa roxburghii* or the microbial agent with tannin samples.

Optionally, specific steps are as follows:

inoculating the tannin-degrading strain SL006 from *Rosa roxburghii* or the microbial agent into a culture medium containing tannin samples for fermentation culture of 5-10 days (d).

Optionally, the culture medium includes a Czapek Dox medium, with starch being used as a carbon source and peptone being used as a nitrogen source; and conditions for the fermentation culture are: pH 7-11, and temperature of 15-30 degrees Celsius (°C).

Optionally, the culture medium includes a solid culture medium of *Rosa roxburghii* pomace; and conditions for the fermentation culture are: pH 7-11, and temperature of 15-30 °C.

Optionally, the solid culture medium of *Rosa roxburghii* pomace is prepared by adding 5-7 weight percentage (wt %) of auxiliary materials and 0.3-0.5 wt % of urea into the *Rosa roxburghii* pomace.

Optionally, the auxiliary materials include one or more of soybean flour, corn flour, rice bran and wheat bran.

Optionally, the tannin samples include *Rosa roxburghii* pomace containing tannin.

The present application discloses the following technical effects:

the strain *Penicillium adametzioides* SL006 shows a high tannin degradation efficiency of up to 98.31% and therefore serves as an efficient tannin-degrading engineering strain;

the strain *Penicillium adametzioides* SL006 shows optimal suitability for mycelial growth and tannin degradation at 30 °C and pH 11; however, the nutritional conditions to satisfy the degradation of tannin and mycelial growth of strain SL006 vary significantly, and the highest rate of tannin degradation is achieved when the carbon and nitrogen sources are starch and peptone, respectively, and the optimal conditions for mycelial growth are glucose and urea as carbon and nitrogen sources, respectively, and the appropriate composition of carbon and nitrogen sources are selected according to the purpose of cultivation for the industrial utilization of the strain;

the strain *Penicillium adametzioides* SL006 applied directly in the fermentation of *Rosa roxburghii* pomace shows low efficiency, yet with 5% soybean powder added, the degradation of tannins in *Rosa roxburghii* pomace by strain SL006 is highly promoted, with the degradation efficiency of tannins reaching 95.24% after 8 d of fermentation; and according to the present application, *Penicillium adametzioides* SL006 from moldy *Rosa roxburghii* pomace is isolated, purified and screened, which has high efficient degradation efficiency to tannin; through experimental verification, the degradation efficiency of screened *Penicillium adametzioides* SL006 to tannin is as high as 98.31%, while by improving the fermentation conditions and formulations, the degradation efficiency of SL006 to tannin within *Rosa roxburghii* pomace reaches higher than 95%, which is of great significance in improving quality of organic fertilizer fermentation of *Rosa roxburghii* pomace.

BRIEF DESCRIPTION OF THE DRAWINGS

For a clearer description of the technical schemes in the embodiments or prior art of the present application, the accompanying drawings to be used in the embodiments are briefly described hereinafter, and it is obvious that the accompanying drawings in the description hereinafter are only some of the embodiments of the present invention, and that for the person of ordinary skill in the field, other accompanying drawings may be obtained based on these drawings without creative labor.

DETAILED DESCRIPTION OF THE EMBODIMENTS

Figure 1:
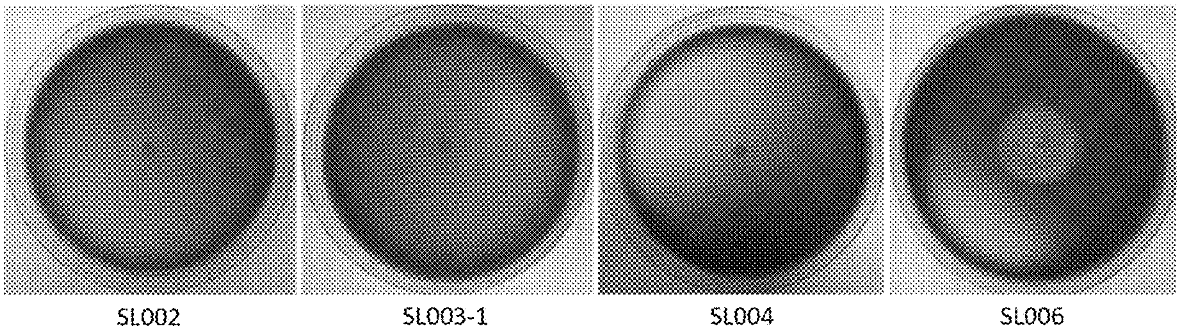
FIG. 1 shows results of initial screening of tannin-degrading strain from *Rosa roxburghii* pomace.

Various exemplary embodiments of the present application are now described in detail, and this detailed description should not be considered as a limitation of the present application, but should be understood as a rather detailed description of certain aspects, characteristics and embodiments of the present application.

It should be understood that the terminology described in the present application is only for describing specific embodiments and is not used to limit the present application. In addition, for the numerical range in the present application, it should be understood that each intermediate value between the upper limit and the lower limit of the range is also specifically disclosed. The intermediate value within any stated value or stated range and every smaller range between any other stated value or intermediate value within the stated range are also included in the present application. The upper and lower limits of these smaller ranges can be independently included or excluded from the range.

Unless otherwise specified, all technical and scientific terms used herein have the same meaning as commonly understood by one of ordinary skill in the art to which this present application relates. Although the present application only describes the preferred methods and materials, any methods and materials similar or equivalent to those described herein may also be used in the practice or testing of the present application. All documents mentioned in this specification are incorporated by reference to disclose and describe methods and/or materials related to the specification. In case of conflict with any incorporated document, the contents of this specification shall prevail.

It is obvious to those skilled in the art that many improvements and changes can be made to the specific embodiments of the present application without departing from the scope or spirit of the present application. Other embodiments will be apparent to the skilled person from the description of the present application. The description and embodiments of the present application are exemplary only.

The terms "including", "comprising", "having" and "containing" used in this specification are all open terms, which means including but not limited to.

Embodiment 1 Isolation and Primary Screening of Tannin-Degrading Bacteria (1) Preparation of a 1% tannin sterile solution: 10 grams (g) of tannin is dissolved in 1,000 milliliters (mL) of warm distilled water, and stirred with a magnetic heating stirrer for 30 minutes (min) for fully dissolution, followed by filtering and sterilizing twice with a 0.22 micrometer (μm) sterile microporous membrane in an ultra-clean workbench to prepare a 1% tannin sterile solution, then the solution is stored in the dark at 5 degrees Celsius (°C) for later use.

(2) Preparation of screening medium for tannin-degrading bacteria: 4.38 g $KH_2PO_4$, 8.76 g $(NH_4)_2SO_4$, 18.00 milligrams (mg) $MnCl_2·6H_2O$, 880.00 mg $MgSO_4·7H_2O$, 88.00 mg $CaCl_2$), 120.00 mg $FeSO_4·7H_2O$, 8.80 mg $NaMoO_4·2H_2O$, 40.00 mg bromophenol blue and 20.00 g agar are weighed respectively, and dissolved in 1,000 mL of distilled water, and the pH is adjusted to 5.5 with 1.0 molar per liter (mol/L) HCl, then sterilized at 121 °C for 15 min; the sterilized medium is cooled to about 55 °C, then 10 mL of 1% tannin sterile solution is added, followed by mixing well and pouring it into a petri dish with diameter of 9 centimeters (cm) to prepare a screening plate.

(3) Isolation and primary screening of tannin-degrading bacteria: the moldy *Rosa roxburghii* pomace fruit pomace and fruit pieces are selected, and the small pieces of tissue are inoculated in potato dextrose agar (PDA) medium by a three-point method, and cultured at 25 °C for 24 hours (h)-48 h; then the edges of the colonies are cut, and the purified strains are obtained by consecutive purification for later use; the purified strains are inoculated in the plate center of tannin-degrading bacteria screening medium by single-spot inoculation with a 6 mm hole puncher, and then incubated at 25 °C for 6 d in the dark to observe and measure the degree of transparency and the width (in mm) of the hyaline circle around the colonies to evaluate the capability of tannin decomposition of the strains.

A total of 26 fungal strains are isolated from moldy *Rosa roxburghii* pomace, but only four strains, including SL002, SL003-1, SL004 and SL0066, have transparent halos around the colonies (see FIG. 1), among which the degradation halo of strain SL006 is the most obvious and has the largest diameter, indicating that the tannin degradation capability of strain SL006 is the strongest.

Embodiment 2 Re-Screening of Tannin-Degrading Bacteria (1) Preparation of a 0.1% tannin standard solution: 0.250 g of tannin standard is accurately weighed and dissolved in 200 mL of warm distilled water, and fully stirred with a magnetic stirrer for 30 min, then fixed with a 250 mL volumetric flask to a constant volume, followed by filtering with a 0.22 μm microporous membrane to remove insoluble particles to obtain a 0.1% tannin standard solution, which is stored at 5 °C in the dark for later use.

(2) Preparation of $FeCl_3$ color developer: 0.162 g of $FeCl_3$ is weighed and dissolved in 100 mL of 0.01 mol/L HCl and kept at 5 °C away from light for later use.

(3) Plotting of tannin standard curve: 0.00, 0.02, 0.04, 0.06, 0.08 and 0.1 mL of 0.1% tannin standard solutions are aspirated respectively and added into 6 clean test tubes, and then 6 mL of $FeCl_3$ color developer is added quickly and sequentially, then the absorbance value at 530 nano-meters (nm) is read by a spectrophotometer after reaction of 30 min at room temperature, and the final volume (V) of tannin is taken as the horizontal coordinates, the absorbance value ($A_{530}$) is taken as the vertical coordinates. Three replicates are arranged.

(4) Preparation of tannin potato dextrose (PD) liquid culture medium: 200 g of potato is weighed and added to 1 L of water and boiled for 30 min, then filtered to obtain a filtrate, to which 20 g of dextrose is added, and then replenished to 1,000 mL with water to obtain the PD liquid culture medium; 90 mL of PD liquid medium is loaded into a 250 ml conical bottle and sterilized at 121 °C for 15 min; after the PD liquid is cooled down, 10 mL of 1% aseptic tannin solution is added, and the mixture is fully mixed for later use.

(5) Re-screening of tannin-degrading bacteria: the strains obtained by primary screening are activated by PDA plate, and then three small 6 mm bacteria cakes are introduced into 100 mL of PD liquid medium with tannin, with oscillation culture at 170 revolutions per minute (r/min) and 25 °C; after 6 d, the fermentation products are filtered by double gauze and centrifuged at high speed of 10,000 r/min for 5 min, and the 0.1 mL of the supernatant is added into 6 mL of color developer $FeCl_3$, and the absorbance value is read at 530 nm by spectrophotometer after reaction of 30 min; a control is set up with the addition of 0.1 mL of deionized water, and 3 replicates are arranged; the measured absorbance value is then substituted into the standard curve to calculate the content, and finally the tannin degradation efficiency (%) is calculated as: tannin degradation efficiency (%)=(average content of tannin in the control fermentation broth−average content of tannin in the fermentation broth of the strain)× 100/average content of tannin in the control fermentation broth.

Figure 2:
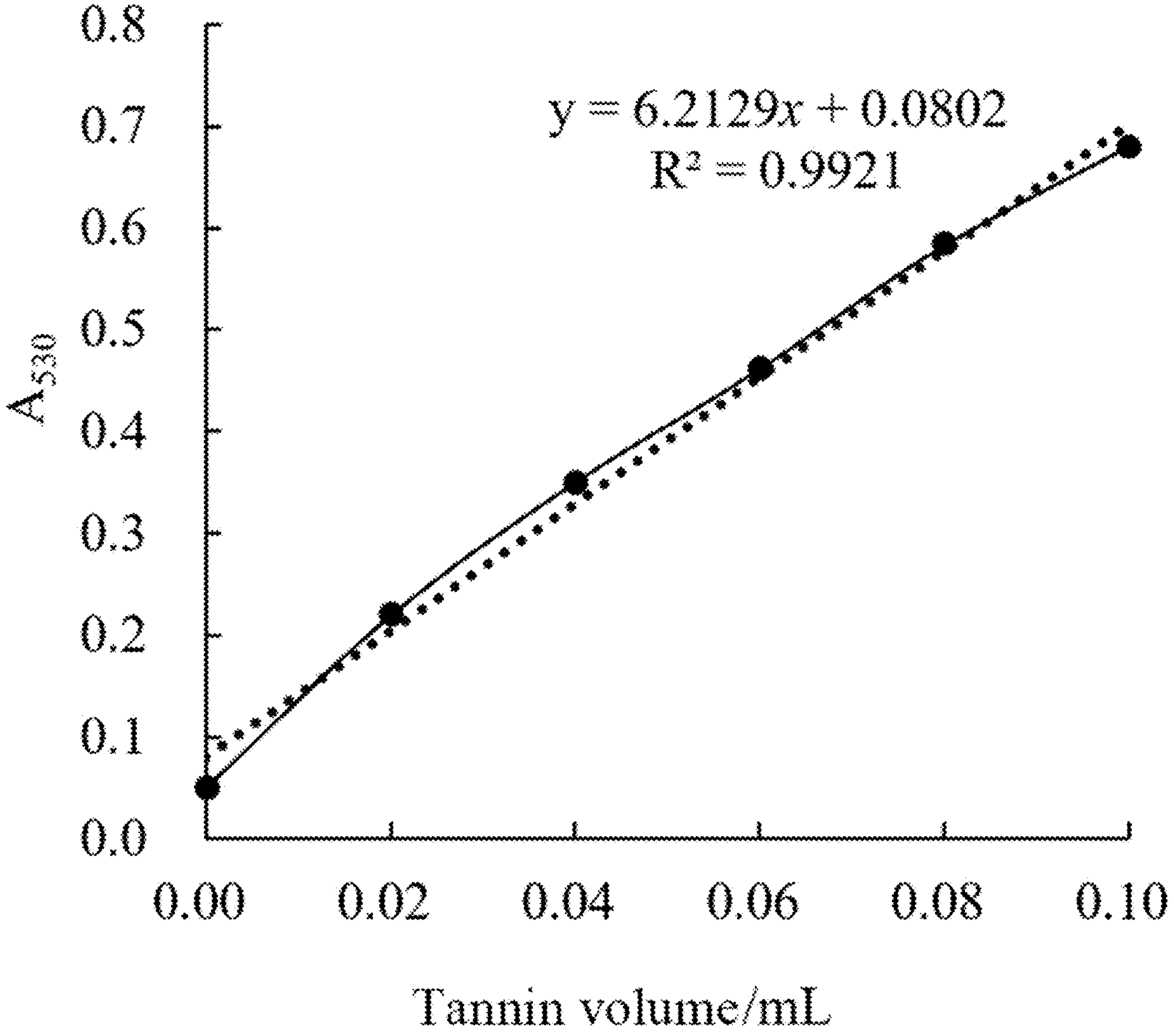
FIG. 2 is a tannin standard curve.

The tannin standard curve constructed by $FeCl_3$ colorimetric method is shown in FIG. 2, it can be seen that the absorbance value of the reaction system at 530 nm is increasing with the rising of tannin content within the set concentration gradient range, and the linear regression equation is $y=6.2129x+0.0802$, the $R^2$ value reaches 0.9921, and the linearity is up to the requirement.

Figure 3:
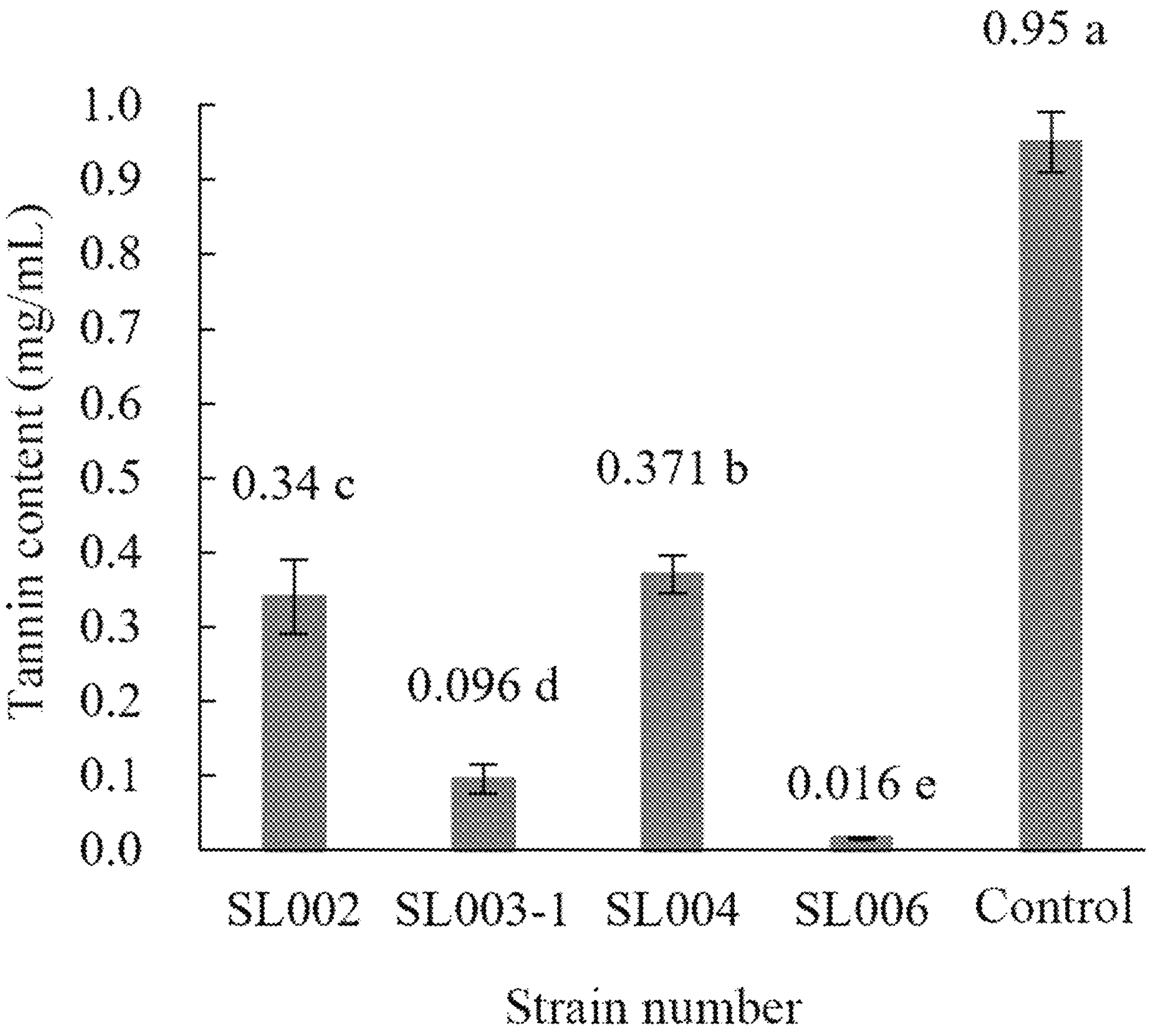
FIG. 3 shows tannin degradation performances of four strains.
Figure 4A:
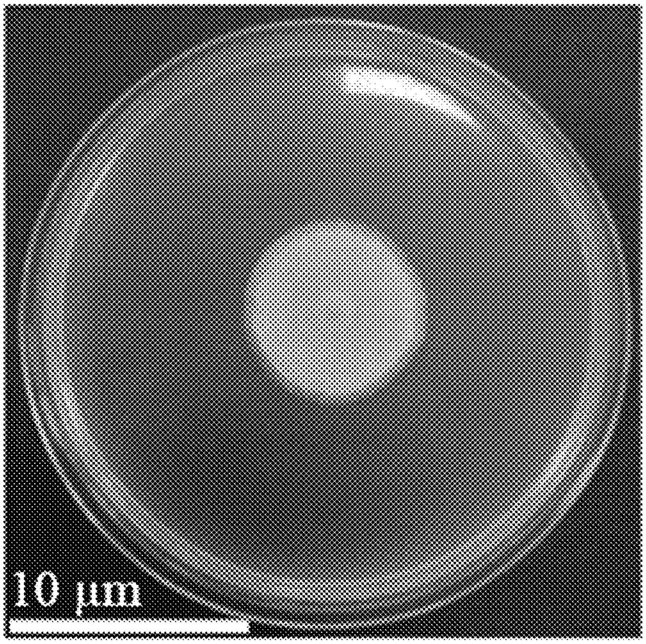
FIG. 4A is a front view of *Penicillium adametzioides* SL006, with scale=10 micrometers (μm).
Figure 4B:
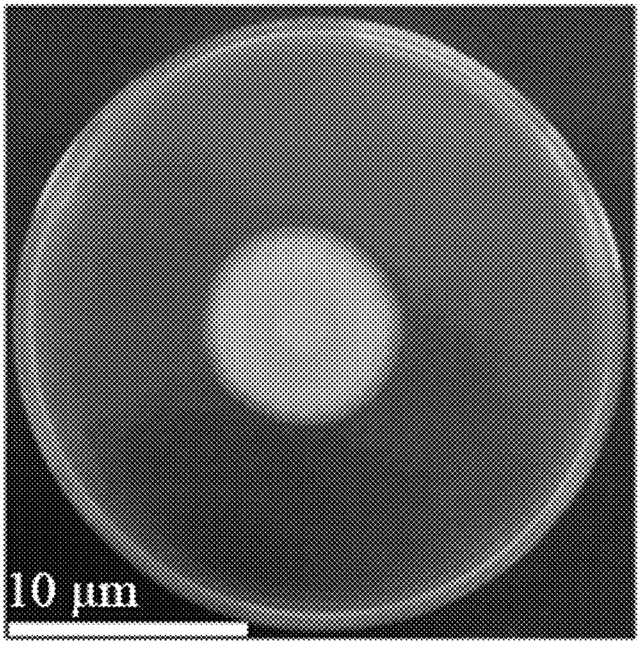
FIG. 4B is a back view of the *Penicillium adametzioides* SL006, with scale=10 μm.
Figure 4C:
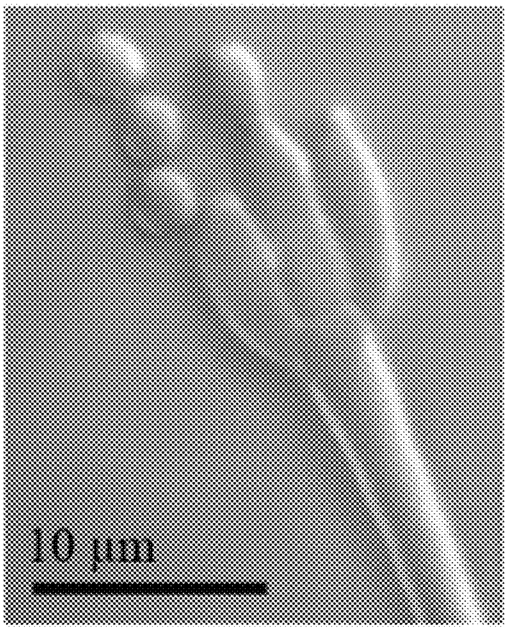
FIG. 4C shows a broom branch of the *Penicillium adametzioides* SL006, with scale=10 μm.
Figure 4D:
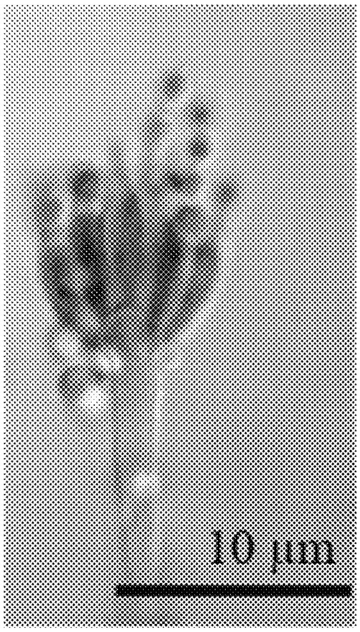
FIG. 4D shows a broom branch of the *Penicillium adametzioides* SL0066, with scale=10 μm.
Figure 4E:
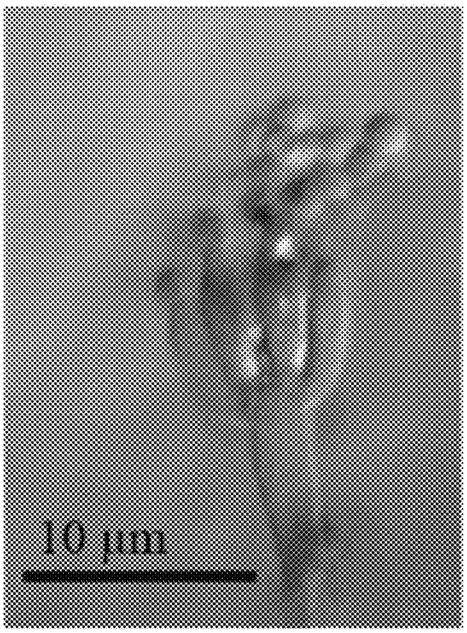
FIG. 4E shows a broom branch of the *Penicillium adametzioides* SL0066, with scale=10 μm.
Figure 4F:
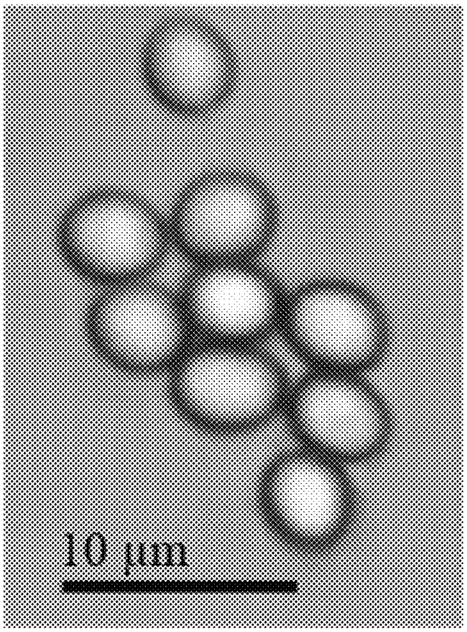
FIG. 4F shows conidia of the *Penicillium adametzioides* SL0066, with scale=10 μm.
Figure 4G:
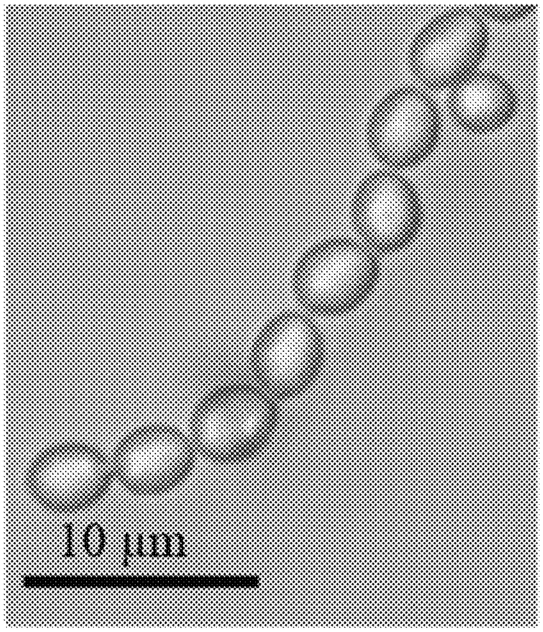
FIG. 4G shows conidia of the *Penicillium adametzioides* SL0066, with scale=10 μm.
Figure 4H:
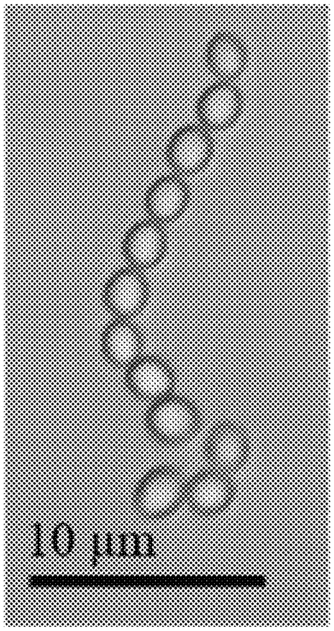
FIG. 4H shows conidia of the *Penicillium adametzioides* SL0066, with scale=10 μm.
Figure 4I:
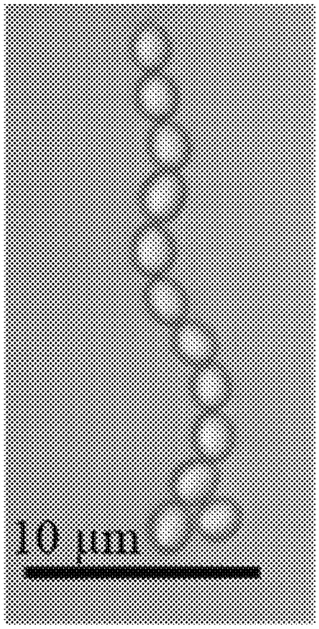
FIG. 4I shows conidia of the *Penicillium adametzioides* SL0066, with scale=10 μm.

The tannin degradation capabilities of the four strains obtained in the initial screening are illustrated in FIG. 3, where the difference in the degradation capabilities of the four strains reaches a significant level, and after the four strains are cultured in tannin PD liquid medium for 6 d, the degradation efficiency of strain SL006 reaches as high as 98.31%, which is a very desirable effect in the degradation of tannin.

Embodiment 3 Morphological Identification of Tannin-Degrading Strain SL006

The mycelium of the strain is picked with a sterile inoculation needle and inoculated in the center of the PDA plate by the single-spot method, and then incubated at 25 °C under natural light for 7 d to observe the color of the colony on the front and back sides and measure the diameter of the colony by the criss-cross method; then the strain is cultured by insert culture method, and the morphological structure of the strain is observed and measured in Olympus BX53 microscopic imaging system.

The morphological characteristics of strain SL006 are shown in FIG. 4A-FIG. 4I; the colonies after 7 d of incubation at 25 °C on PDA are 26-33 mm in diameter (29.25±3.04 mm, n=6), with whorls and slightly raised centers, compact and thin quality and light green on the front side, and orange-yellow on the back side, and darker in the center (FIG. 4A, FIG. 4B); conidiophores appear in the apical part of aerial mycelium, broom-like branches in a single whorl, ampoule-shaped stalks, each whorl 3-8 or more, 7.92-12.54×2.27-3.44 μm in size ('x=10.55±1.27× 2.78±0.31 μm, n=30) (FIG. 4C, FIG. 4D, and FIG. 4E); conidia are in chains at the apical end of stalks, ellipsoidal or rounded, with size of 2.15-3.91×1.71-2.61 μm ('x=2.82±0.36×2.24±0.21 μm, n=30), smooth surface (FIG. 4F—FIG. 4I), and with typical morphological features of *Penicillium adametzioides*.

Embodiment 4 Molecular Identification of Tannin-Degrading Strain SL006

The test strain is inoculated on PDA plate medium and cultured at a constant temperature of 25 °C for 10 d; then the mycelium is scraped and the DNA of the strain is extracted by a modified cetyltrimethylammonium bromide (CTAB) method (for the modified CTAB method, please refer to ZHANG Yinghui, WEI Dongsheng, XING Laijun, et al. A Modified Method for Isolating DNA from Fungus [J]. Microbiology China, 2008, No. 199(03):466-469.); the amplified target sequences are β-tubulin gene (TUB2) and the internal transcribed spacer (ITS) respectively.

Primers Selected for β-Tubulin Gene:

```
BT2A:
                                        (SEQ ID NO: 1)
5'-GGTAACCAAATCGGTGCTGCTTTC-3';

BT2B:
                                        (SEQ ID NO: 2)
5'-ACCCTCAGTGTAGTGACCCTTGGC-3'.
```

Primers Selected for ITS Sequences:

```
ITS1:
                                        (SEQ ID NO: 3)
5'-TCCGTAGGTGAACCTGCGG-3';

ITS4:
                                        (SEQ ID NO: 4)
5'-TCCTCCGCTTATTGATATGC-3'.
```

PCR reaction system (25 μL): 1 μL forward primer, 1 μL reverse primer, 2×Taq PCR Mas-ter Mix×12.5 μL, 8.5 μL $ddH_2O$ and 2 μL template.

The PCR reaction conditions for amplification of β-tubulin are as follows: pre-denaturation at 95 °C for 4 min; denaturation at 94 °C for 48 seconds (s); annealing at 55 °C for 48 s; extension at 72 °C for 60 s; 35 cycles; and extension at 72 °C for 5 min; and for amplification of ITS, the PCR reaction conditions are as follows: pre-denaturation at 94 °C for 3 min; denaturation at 95 °C for 30 s; annealing at 55 °C for 30 s; extension at 72 °C for 60 s; 35 cycles; and finally, extension at 72 °C for 5 min.

After amplification, the amplified products are detected by 1% agarose gel electrophoresis, and then purified and sequenced by Beijing Tsingke Biotechnology Co., Ltd.; the obtained sequences are input into basic local alignment search tool (BLAST) of GenBank for homologous sequence search to find strains with high similarity, and the two gene sequences are spliced by Sequence Matrix 1.7.8, and the results of the splicing are used to construct a phylogenetic tree by the Maximum likelihood (ML) method using software MEGA 11 to determine the taxonomic status of the strains.

β-Tubulin Gene Sequence:

```
                                        (SEQ ID NO: 5)
CTGCTTTCTGGTACGTGTTTCCACCCATCAAATGTTGACACCCATTGAA

ACTTTTTTACTAACTACCTTATAGGCAGAACATTGCCTCCGAGCACGGT

CTCGATGGTGATGGACAGTAAGTTCTTTGATTCGAGTCGATTGGTATAT

ATGGTGGGAATGGCGGTCTGATATTTTTTTTCTAGCTTCACCGGCCAGT

CCGACCTCCAGCTGGAGCGTATGAACGTCTACTTCAACCACGTAAGTGT

GGAATTGATCCCTCGAGCCATTCGATATTGGCTAATATTTGGATTGTTT

ACAGGCCAGCGGTGACCGTTACGTTCCCCGTGCCGTCCTGGTCGATTTG

GAGCCCGGTACCATGGACGCTGTCCGTGCCGGTCCTTTCGGCAAGCTTT

TCCGTCCCGACAACTTCGTTTTCGGTCAGTCCGGTGCTGGTAACAACTG

GGCCAAGGGT.
```

ITS Sequence of Strain:

```
                                        (SEQ ID NO: 6)
CATTACTGAGTGAGGGCCTTCGGGTCCAACCTCCCACCCGTGTCTATTG

TACCATGTTGCTTCGGCAGGCCCGCCTTATGGCCGCCGGGGGCTAACCG

CCCCGGGCCCGCGCCTGCCGAAGACCCCTCTGAACGCTGTCTGAAGATT

GCCGTCTGAGCGAAACATATAAATTATTTAAAACTTTCAACAACGGATC

TCTTGGTTCCGGCATCGATGAAGAACGCAGCGAAATGCGATAACTAATG

TGAATTGCAGAATTCAGTGAATCATCGAGTCTTTGAACGCACATTGCGC

CCTCTGGTATTCCGGAGGGCATGCCTGTCCGAGCGTCATTGCTGCCCTC

AAGCCCGGCTTGTGTGTTGGGTCTCGTCCCCCCCGGGGGACGGGCCCGA

AAGGCAGCGGCGGCACCGTGTCCGGTCCTCGAGCGTATGGGGCTTTGTC

ACCCGCTCTGTAGGCCCGGCCGGCGCCTGTCGACCCCCAATCTATTTTT

TTCAGGTTGACCTCGGATCAGGTAGGGATACCCGCTGAACTTAAGCATA

T.
```

Figure 5:
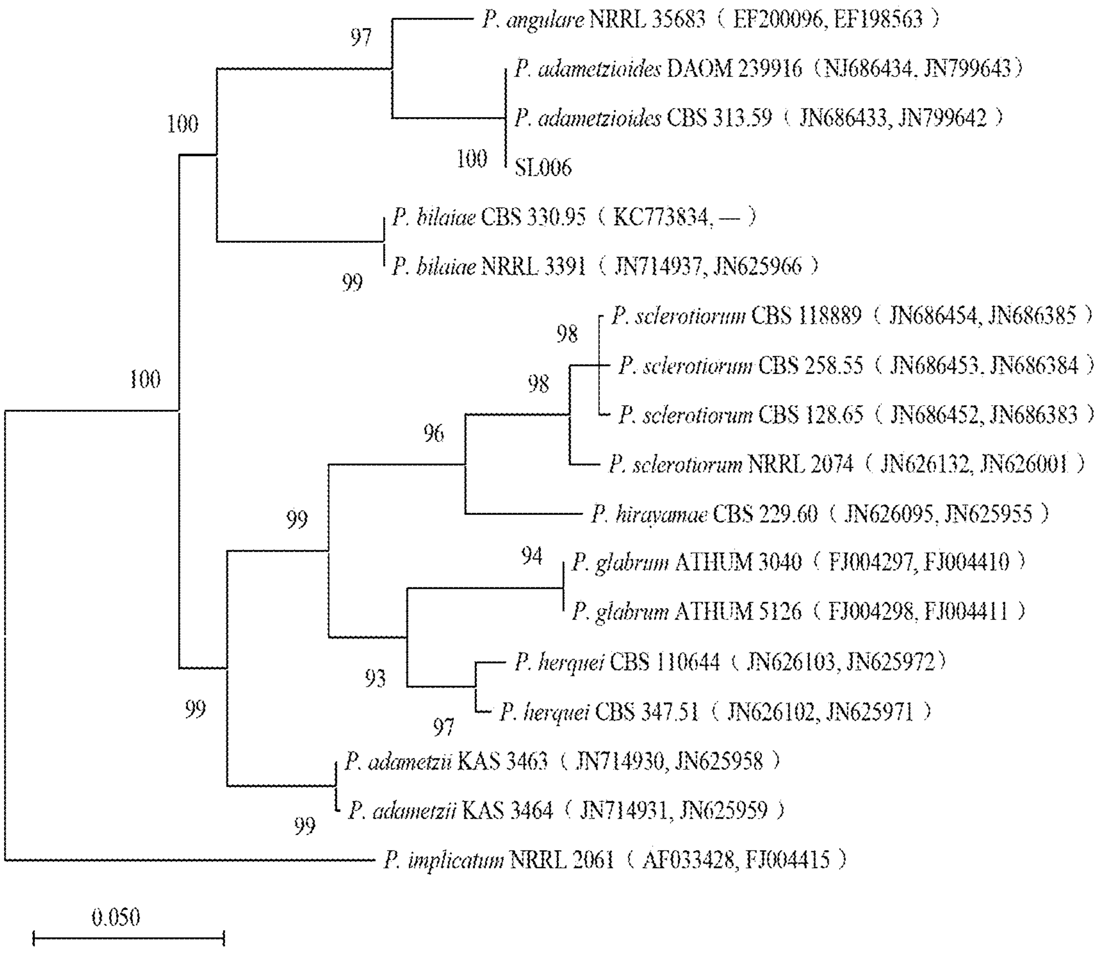
FIG. 5 is a phylogenetic tree constructed by maximum likelihood method based on internal transcribed spacer (ITS) and β-tubulin polygene sequences.

According to ITS and β-tubulin sequences of strain SL006, 17 sequences with high homology are downloaded from GenBank. The ML phylogenetic tree (FIG. 5) is constructed using MEGA 11 with *Penicillium implicatum* NRRL 2061 as the outgroup. Strain SL006 is clustered into one unit with *Penicillium adametzioides* with high support of 100%. Therefore, strain SL006 is identified as *Penicillium adametzioides* based on morphology and ITS and ß-tubulin sequence analysis.

Preservation of Strain SL006

Strain SL006 is named as *Penicillium adametzioides*, and is preserved in China Center for Type Culture Collection (CCTCC for short, address: Wuhan University, China), with a preservation number of CCTCC NO: M 20221946.

Embodiment 5 Screening of Fermentation Conditions of Tannin-Degrading Strain SL006

(1) Preparation of strain seed liquid: 3 pieces of 6 mm bacterial cake are inoculated in 100 mL Czapek Dox liquid medium, followed by oscillation culture for 48 h at 25 °C and 160 r/min to obtain the seed liquid for later use.

(2) Effect of temperature on growth and tannin degradation of tannin-degrading strain SL006: after inoculation of 2 mL of seed liquid in 100 mL of Czapek Dox liquid medium containing 0.1% tannin and then placed in 160 r/min shaker at 15 °C, 20 °C, 25 °C, 30 °C, 35 °C and 40 °C, respectively, the growth of mycelium (in g) of tannin-degrading strain and the content of tannin in the liquid medium under treatment of different temperatures is measured after 5 d, with 3 replicates arranged; determination of mycelial growth (in mg): the gauze is cut into 10×10 cm squares, baked in an oven to a constant weight and then measured in terms of dry weight of the gauze (mg); the cultured bacterial liquid is poured onto three layers of gauze of known weight for filtration, and the mycelium and gauze are collected and dried together at 60 °C to a constant weight and measured in terms of total dry weight (mg); mycelial growth (mg)=total dry weight of gauze and mycelium-dry weight of gauze; the content of tannin in the liquid medium is measured as in Embodiment 2.

(3) Effects of different pH values on mycelial growth and tannin degradation: first, the pH of the liquid Czapek Dox medium containing 0.1% tannin is adjusted to a gradient of 5, 6, 7, 8, 9, 10, 11, 12, and 13 with 1 mol/mL of HCl or NaOH, respectively, and 2 mL of seed liquid is inoculated in 100 mL of the medium of different pH, and uniformly placed in the optimal temperature and 160 r/min shaker derived in (2) for cultivation, and the rest of steps are the same as those in (2).

(4) Effect of carbon sources on mycelial growth and tannin degradation: sucrose in Czapek Dox liquid medium containing 0.1% tannin is replaced with starch, glucose, fructose, maltose, lactose, glycerol in the same mass, and the pH is adjusted to the optimum pH value derived in (3); 2 mL of seed liquid is inoculated in 100 mL of the medium and uniformly placed in the optimum temperature derived in (2), incubated in a shaker at 160 r/min, and the remaining steps are the same as those in (2).

(5) Effects of nitrogen sources on mycelial growth and tannin degradation: sodium nitrate in Czapek Dox liquid medium containing 0.1% tannin is replaced by urea, peptone, ammonium nitrate, yeast powder in the same mass, and the pH is adjusted to the optimum pH value derived in (3); 2 mL of seed liquid is inoculated in 100 mL of the medium and uniformly placed in the optimum temperature derived in (2), incubated in a shaker at 160 r/min, and the remaining steps are the same as those in (2).

The treatment effects of different temperatures, the pH values, carbon sources and nitrogen sources on the tannin degradation efficiency and mycelial growth of strain SL006 reach a significant level (FIG. 6A-FIG. 6D). The tannin degradation efficiency and mycelial growth of strain SL006 at 30 °C are significantly higher than those of other temperature treatments (FIG. 6A), the highest tannin degradation efficiency of the strain is obtained at pH 7-11, and the largest mycelial growth of the strain is observed at pH 11 (FIG. 6B), indicating that mycelial growth and tannin degradation of strain SL006 is best optimized at 30 °C and pH 11.

Figure 6A:
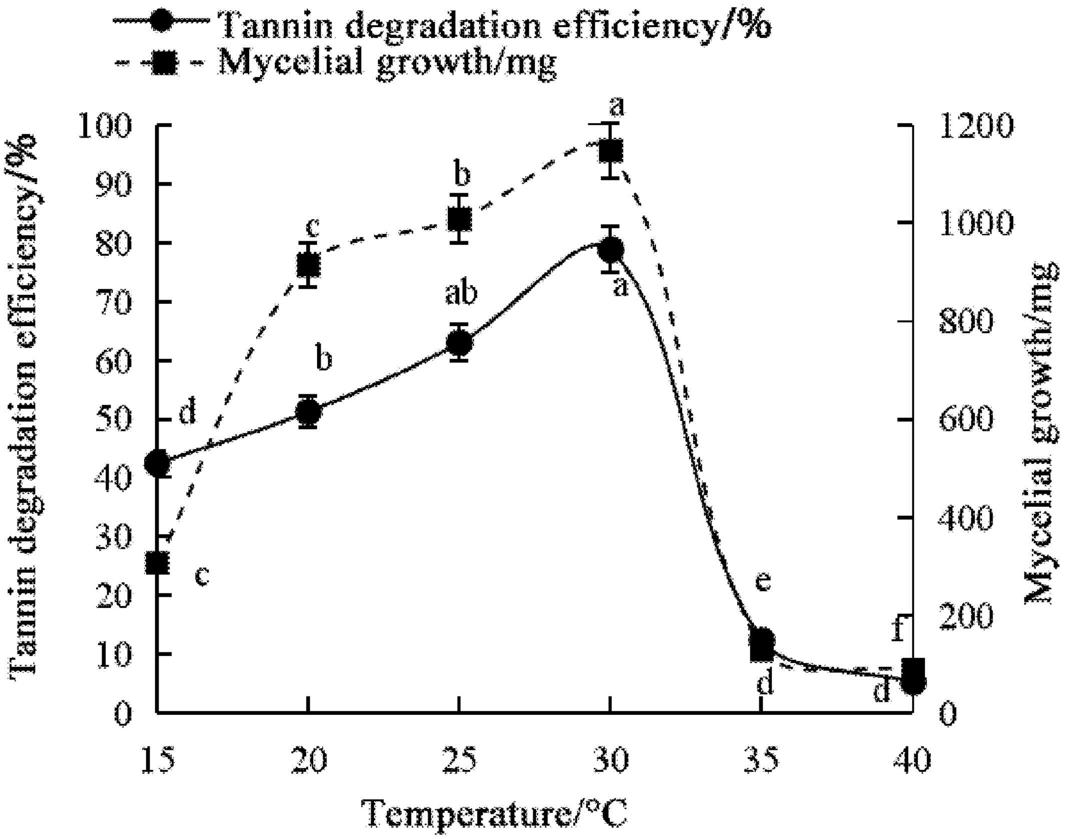
FIG. 6A shows effects of different temperatures on mycelial growth and tannin degradation of strain SL006.
Figure 6B:
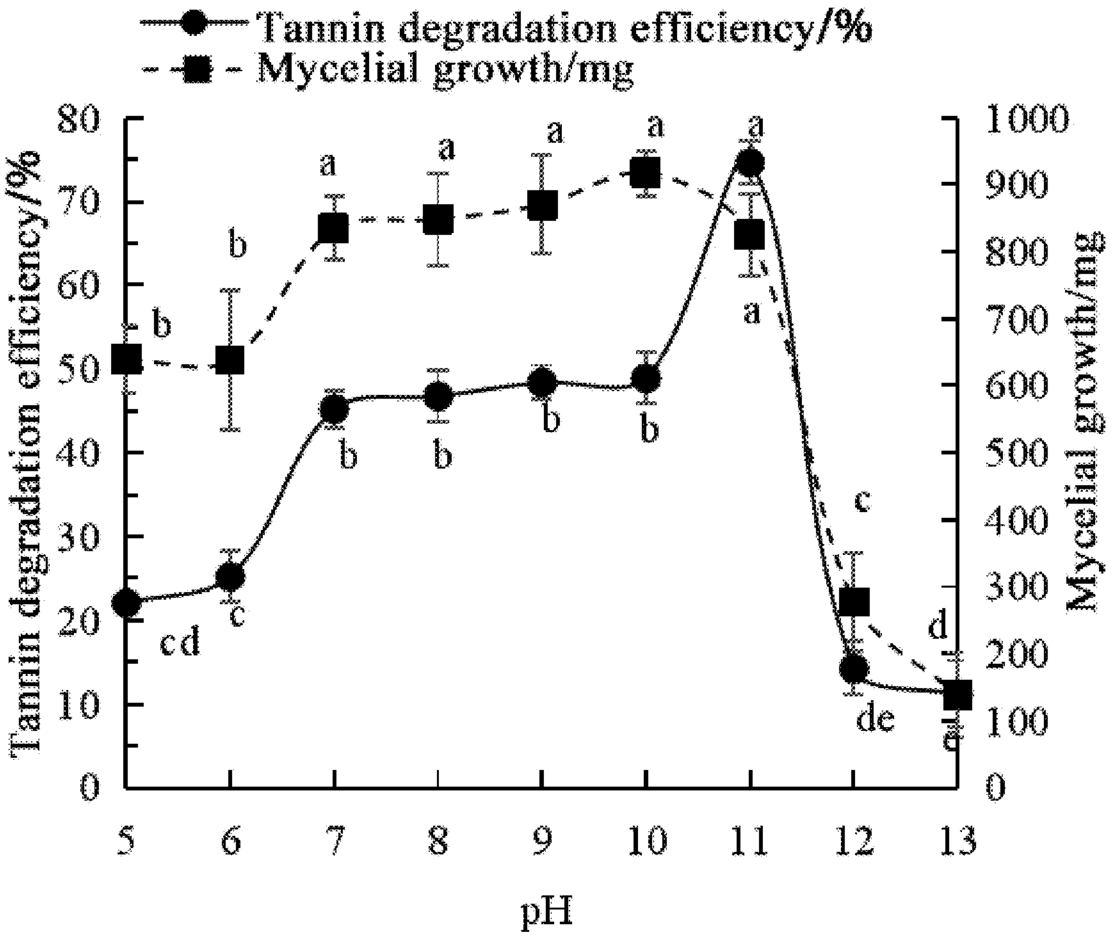
FIG. 6B shows effects of different pH values on mycelial growth and tannin degradation of strain SL006.
Figure 6C:
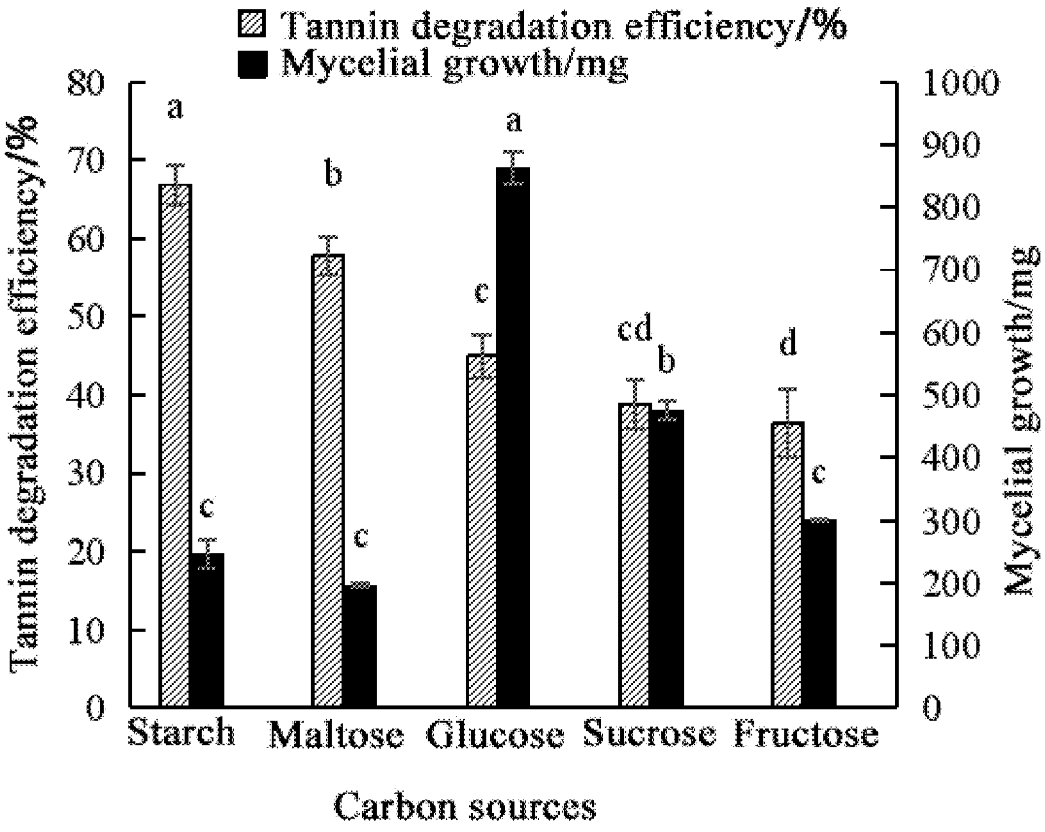
FIG. 6C shows effects of different carbon sources on mycelial growth and tannin degradation of strain SL006.
Figure 6D:
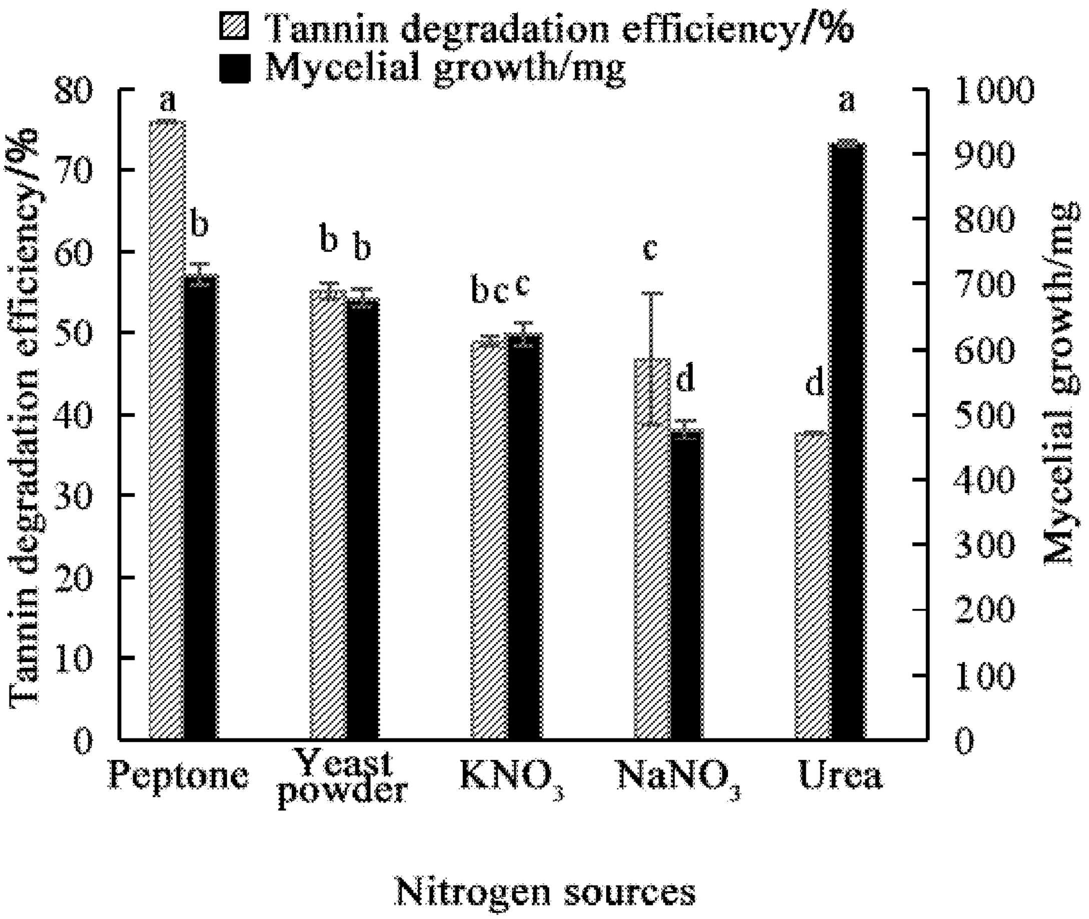
FIG. 6D shows effects of different nitrogen sources on mycelial growth and tannin degradation of strain SL006.

The tannin degradation efficiency under starch as carbon source is significantly higher than other treatments, followed by maltose and glucose, and sucrose and fructose are the worst; mycelial growth under glucose as carbon source is significantly higher than other treatments, followed by sucrose, and starch, maltose and fructose are the most ineffective (FIG. 6C); The tannin degradation efficiency under peptone as nitrogen source is significantly higher than other nitrogen source treatments, and the highest mycelial growth is observed under urea as nitrogen source (FIG. 6D), which indicates that there are significant differences in the nutrient conditions to satisfy the degradation of tannin and the mycelial growth of strain SL006, and that the tannin degradation rate is the highest when the carbon and nitrogen sources are starch and peptone, respectively, and that the growth of the mycelium is best suited when the carbon and nitrogen sources are glucose and urea, respectively. In the industrial utilization of strains, appropriate carbon and nitrogen source compositions are available for selection according to the purpose of cultivation.

Embodiment 6 Study on the Degradation Characteristics of Tannin in *Rosa roxburghii* Pomace by Tannin-Degrading Bacteria (1) preparation of solid culture medium of *Rosa roxburghii* pomace and inoculation of degrading bacteria: fresh *Rosa roxburghii* pomace is dried to a constant weight at 50 °C, and the pomace is finely ground with a ceramic mortar and sieved through a 40-mesh nylon sieve; respectively, 5% of wheat bran flour, cornstarch, soybean flour with a fineness of 40 mesh and 0.3% of urea are added to the *Rosa roxburghii* pomace, with the pure *Rosa roxburghii* pomace as the control, and 5 mL of deionized water is added to fully mix the pomace and adjust the pH to the optimal pH value as derived from Embodiment 5, and placed in a petri dish with a 9 mm diameter for sterilization at 121 °C for 5 min; after cooling, each dish is respectively inoculated with 0.5 mL of seed liquid of the tannin-degrading bacteria; each treatment is inoculated with 10 petri dishes and repeated 3 times; after mixing well, the pomace is pressed flat, covered with plastic wrap and placed in the optimal temperature derived from Embodiment 5 for incubation, and the tannin content in the pomace is sampled and measured once every 2 d until the 10th d.

(2) Determination of tannin content in *Rosa roxburghii* pomace: the fermented pomace is dried at 50 °C to a constant weight, ground in a ceramic mortar and passed through a 100 mesh nylon sieve; 1.00 g of pomace powder is accurately weighed into a triangular flask and extracted with 25 mL of 20% ethanol solution at 25 °C with shaking at 160 r/min for 120 min; the extract is centrifuged at 8,000 r/min for 5 min, and 0.1 mL of the supernatant is dropped into 6 mL of $FeCl_3$ color developer, and the absorbance value at 530 nm is read by a spectrophotometer after the reaction at room temperature for 30 min; the tannin content (%) in the extract of each treatment is determined as in Embodiment 2. Tannin degradation efficiency (%)=(tannin content of each treatment at 0 d–average tannin content of each treatment at day i)×100 tannin content of each treatment at 0 d. The tannin content of each treatment at 0 d is determined by the same method as in Embodiment 2.

Figure 7A:
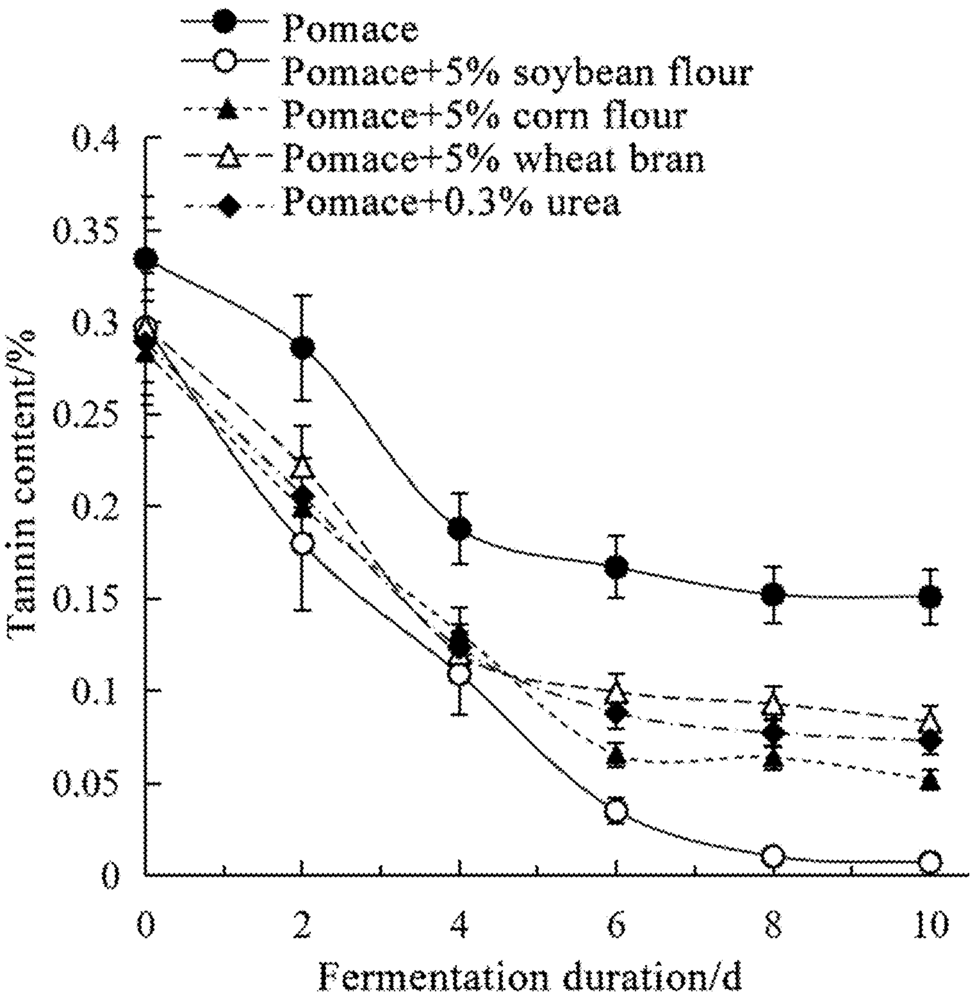
FIG. 7A shows tannin content of each treatment.
Figure 7B:
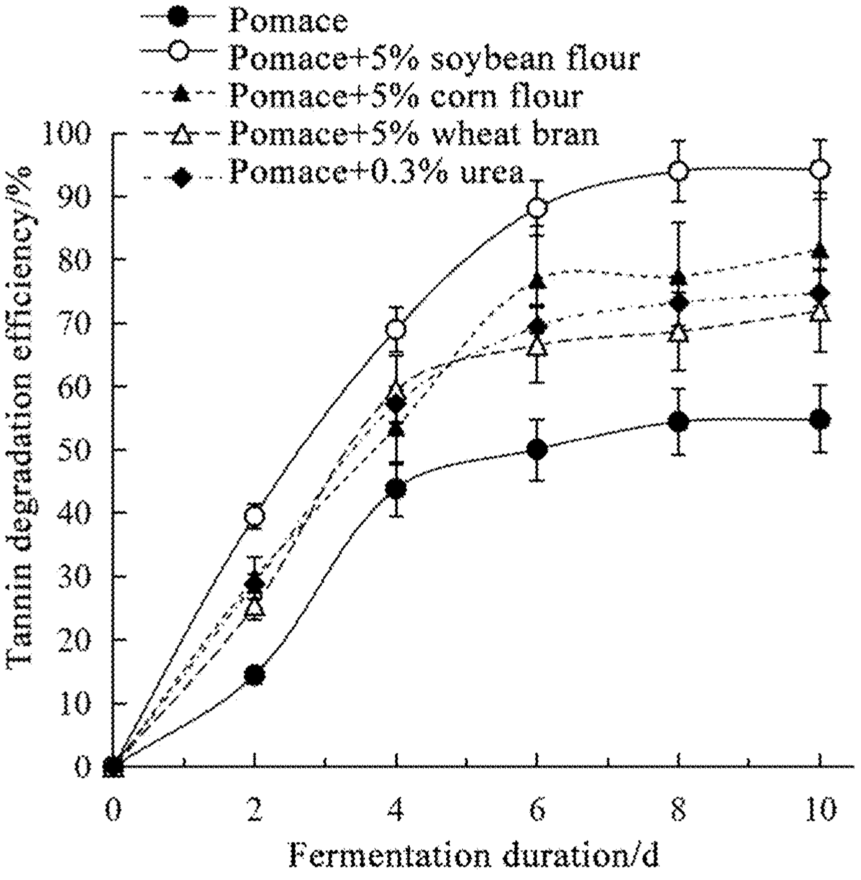
FIG. 7B illustrates tannin degradation efficiencies of each treatment.

Strain SL006 is effective in degrading tannin within the *Rosa roxburghii* pomace (FIG. 7A and FIG. 7B). The tannin content remains stable at the 8th d of fermentation. The degradation efficiency of single *Rosa roxburghii* pomace fermentation is only 54.24% in the 8th d. By adding 5% soybean powder, corn flour, rice bran and wheat bran to the *Rosa roxburghii* pomace, the degradation efficiency of strain SL006 is significantly improved, among which the degradation efficiency of treatment added with 5% soybean powder is the highest, and the degradation efficiency of the strain SL006 reaches 95.24% in the fermentation of the pomace in the 8th d. This indicates that strain SL006 is less efficient when used directly in the fermentation of *Rosa roxburghii* pomace, and the addition of soybean powder with higher nitrogen content promotes the degradation of tannins in *Rosa roxburghii* pomace by strain SL006 with high efficiency.

The above-described embodiments serve only to describe the preferred manner of the present application, and are not intended to limit the scope of the present application. Without departing from the spirit of the design of the present application, the various deformations and improvements made by the persons of ordinary skill in the field of the technical schemes of the present application shall fall within the scope of protection as determined by the claims of the present application.

What is claimed is:

1. A method for degrading tannin, comprising a step of fermenting tannin samples with a strain SL006 from *Rosa roxburghii* pomace, wherein the strain has a taxonomic designation of *Penicillium adametzioides* and has been preserved with the China Center for Type Culture Collection (CCTCC) under preservation No. CCTCC NO: M 20221946, with a deposit date of Dec. 13, 2022.

2. The method for degrading tannin according to claim 1, wherein the step of fermenting is of inoculating the strain SL006 from the *Rosa roxburghii* pomace into a culture medium containing the tannin samples for fermentation culture of 5-10 days.

3. The method for degrading tannin according to claim 2, wherein the culture medium comprises a Czapek Dox medium, with starch used as a carbon source and peptone used as a nitrogen source; and wherein conditions for the fermentation culture are: pH 7-11, and a temperature of 15-30 degrees Celsius.

4. The method for degrading tannin according to claim 2, wherein the culture medium comprises a solid culture medium of *Rosa roxburghii* pomace; and conditions for the fermentation culture are: pH 7-11, and a temperature of 15-30 degrees Celsius.

5. The method for degrading tannin according to claim 4, wherein the solid culture medium of the *Rosa roxburghii* pomace is prepared by adding 5-7 weight percentage of an auxiliary material and 0.3-0.5 weight percentage of urea into the *Rosa roxburghii* pomace.

6. The method for degrading tannin according to claim 5, wherein the auxiliary material is soybean flour.

7. The method for degrading tannin according to claim 1, wherein the tannin samples comprise *Rosa roxburghii* pomace containing tannin.

* * * * *